US009897602B2

(12) United States Patent
Zheng et al.

(10) Patent No.: US 9,897,602 B2
(45) Date of Patent: Feb. 20, 2018

(54) MICROARRAY SUBSTRATE, MICROARRAY, MICROFLUIDIC SYSTEM AND METHODS FOR PREPARING THE SAME

(71) Applicant: The Chinese University of Hong Kong, Hong Kong (CN)

(72) Inventors: Bo Zheng, Hong Kong (CN); Hui Feng, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 598 days.

(21) Appl. No.: 14/446,017

(22) Filed: Jul. 29, 2014

(65) Prior Publication Data
US 2015/0038364 A1 Feb. 5, 2015

Related U.S. Application Data

(60) Provisional application No. 61/859,896, filed on Jul. 30, 2013.

(51) Int. Cl.
*G01N 33/543* (2006.01)
*G01N 33/545* (2006.01)
(Continued)

(52) U.S. Cl.
CPC ....... *G01N 33/54393* (2013.01); *C40B 20/02* (2013.01); *C40B 40/02* (2013.01);
(Continued)

(58) Field of Classification Search
CPC ......... C40B 40/06; C40B 40/04; C40B 40/02; C40B 40/10; C40B 40/08; G01N 33/54393; G01N 33/54353
See application file for complete search history.

(56) References Cited

U.S. PATENT DOCUMENTS 2,230,654 A 2/1941 Plunkett
4,591,570 A 5/1986 Chang
(Continued)

FOREIGN PATENT DOCUMENTS

CN 101530775 A 9/2009
CN 101745327 A 6/2010
(Continued)

OTHER PUBLICATIONS

Sun et al. (Langmuir, 2012, 28:2131-2136).*
(Continued)

*Primary Examiner* — Jeremy C Flinders
(74) *Attorney, Agent, or Firm* — Knobbe Martens Olson & Bear LLP

(57) ABSTRACT

A microarray substrate including a piece of fluoropolymer whose surface is modified with polydopamine, in which the polydopamine forms an array of microspots on the surface of the fluoropolymer piece, and allows immobilization of molecules or cells. A microarray including the substrate, a microfluidic system designed for dispensing reagents onto selected locations on the surface of substrates, and a method for preparing the substrate and the microarray, in which a dopamine solution is dispensed onto the fluoropolymer piece using the microfluidic system, and forms an array of polydopamine microspots serving as the reaction sites for microarray analysis.

23 Claims, 5 Drawing Sheets

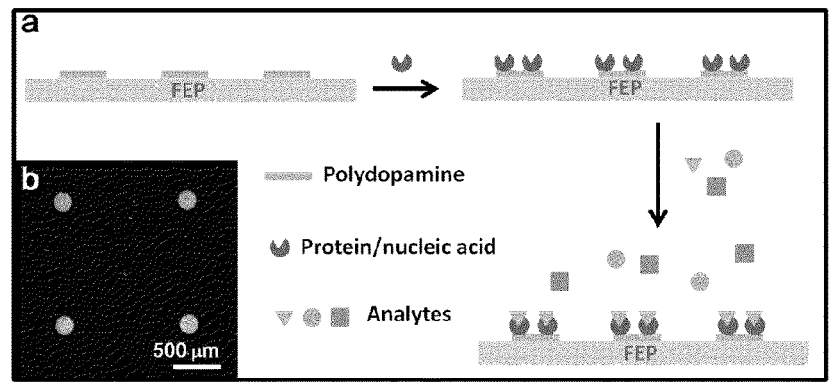

(a). Scheme showing the microarray fabrication and analysis on the polydopamine microspots. (b). Fluorescence image showing the results of using IgG microarray on the fluoropolymer substrate to detect FITC labeled anti-IgG.

(51) Int. Cl.

| | | |
|---|---|---|
| C40B 20/02 | (2006.01) | |
| C40B 40/04 | (2006.01) | |
| C40B 40/02 | (2006.01) | |
| C40B 40/06 | (2006.01) | |
| C40B 40/10 | (2006.01) | |
| C40B 40/08 | (2006.01) | |

(52) U.S. Cl.
CPC ............. *C40B 40/04* (2013.01); *C40B 40/06* (2013.01); *C40B 40/10* (2013.01); *G01N 33/545* (2013.01); *G01N 33/54353* (2013.01); *C40B 40/08* (2013.01)

(56) References Cited

U.S. PATENT DOCUMENTS

| | | |
|---|---|---|
| D308,722 S | 6/1990 | Chang et al. |
| 5,100,777 A | 3/1992 | Chang |
| 2003/0089605 A1 | 5/2003 | Timperman |

FOREIGN PATENT DOCUMENTS

| | | |
|---|---|---|
| CN | 102465119 A | 5/2012 |
| CN | 102614783 A | 8/2012 |
| CN | 102901809 A | 1/2013 |
| WO | WO 01/94946 A2 | 12/2001 |
| WO | WO 2004/039962 A2 | 5/2004 |
| WO | WO 2012/158717 A2 | 11/2012 |

OTHER PUBLICATIONS

Jiang et al. (Langmuir, 2011, 27:14180-14187).*
Jiang et al., Surface Modification of PE Porous Membranes Based on the Strong Adhesion of Polydopamine and Covalent Immobilization of Heparin, Journal of Membrane Science, Aug. 14, 2010, pp. 194-202.
Ku et al., General Functionalization Route for Cell Adhesion on Non-Wetting Surfaces, Biomaterials 31, Jan. 12, 2010, pp. 2535-2541.
Linlin et al., Surface Tailoring of PTFE for Endotheleal Cells Selectivity Based on Polydopamine-Assisted Self-Assembly Monolayer Technique, Acta Polymerica Sinica, Apr. 2010, No. 4, pp. 479-483.
Lynge et al., Polydopamine—A Nature-Inspired Polymer Coating for Biomedical Science, Nanoscale, Dec. 31, 2011, pp. 4916-4928.
Zhou et al., Nanoliter Dispensing Method by Degassed Poly(dimethylsiloxane) Microchannels and its Application in Protein Crystallization, Anal.Chem., Jul. 1, 2007, vol. 79, pp. 4924-4930.
Search Report in Chinese Patent Application No. 2014103649343, dated Oct. 19, 2015.
Cretich et al., "Protein and peptide arrays: recent trends and new directions." *Biomolecular Engineering* 23. 77-88, (2006).
Dreyer et al., "Perspectives on poly (dopamine)." *Chemical Science* 4, pp. 3796-3802 (2013).
Duffy et al., "Rapid prototyping of microfluidic systems in poly (dimethylsiloxane)." *Analytical Chemistry* 70, pp. 4974-4984 (1998).
Hsieh et al., Effective enhancement of fluorescence detection efficiency in protein microarray assays: application of a highly fluorinated organosilane as the blocking agent on the background surface by a facile vapor-phase deposition process, *Analytical Chemistry*, 81, pp. 7908-7916 (2009).
Han et al., Measuring rapid kinetics by a potentiometric method in droplet-based microfluidic devices, Chem. Commun., 48, pp. 1601-1603 (2012).
Lee et al., "Mussel-inspired surface chemistry for multifunctional coatings." *Science* 318, pp. 426-430, (2007).
Kusnezow et al., "Solid supports for microarray immunoassays." *Journal of Molecular Recognition* 16, pp. 165-176 (2003).
Lee et al., "Facile conjugation of biomolecules onto surfaces via mussel adhesive protein inspired coatings." *Advanced Materials* 21, pp. 431-434 (2009).
Kingsmore, Stephen F. "Multiplexed protein measurement: technologies and applications of protein and antibody arrays." *Nature Reviews Drug Discovery* 5(4), pp. 310-321 (2006).
Jeyachandran et al., "Efficiency of blocking of non-specific interaction of different proteins by BSA adsorbed on hydrophobic and hydrophilic surfaces." *Journal of colloid and interface science* 341, pp. 136-142 (2010).
Pirri et al., "Microarray glass slides coated with block copolymer brushes obtained by reversible addition chain-transfer polymerization." *Analytical Chemistry* 78, pp. 3118-3124 (2006).
Rusmini et al., "Protein immobilization strategies for protein biochips." *Biomacromolecules* 8, pp. 1775-1789 (2007).
MacBeath et al., "Printing proteins as microarrays for high-throughput function determination." *Science* 289, pp. 1760-1763 (2000).
Lee et al., "Protein-resistant surfaces prepared by PEO-containing block copolymer surfactants." *Journal of BiomedicalMmaterialsRresearch* 23:3, pp. 351-368 (1989).
Schena, Mark, et al. "Parallel human genome analysis: microarray-based expression monitoring of 1000 genes." *Proceedings of the National Academy of Sciences* 93, pp. 10614-10619 (1996).
Shultz et al., "Optimized Blocking of Porous Nitrocellulose Films for Sensitive Protein Microarrays." *Biotechniques* 54:4, pp. 223-225 (2013).
Vogelstein et al., "Digital PCR." *Proceedings of the National Academy of Sciences* 96, 9236-9241 (1999).
Wiese, Rick. "Analysis of several fluorescent detector molecules for protein microarray use." *Luminescence* 18, pp. 25-30 (2003).
Unger et al., "Monolithic microfabricated valves and pumps by multilayer soft lithography." *Science* 288, pp. 113-116 (2000).
Sethi et al., "New protocol for oligonucleotide microarray fabrication using SU-8-coated glass microslides." *Bioconjugate Chemistry* 21, pp. 1703-1708 (2010).
Nagl et al., "Fluorescence analysis in microarray technology." *Microchimica Acta* 151, pp. 1-21 (2005).
Xia et al., "Soft Lithography." *Angew. Chem. Int. Ed* 37: 550-575 (1998).
Tang et al., "A PDMS viscometer for assaying endoglucanase activity." *Analyst* 136.: 1222-1226 (2011).
Han et al., "A PDMS viscometer for microliter Newtonian fluid." *Journal of Micromechanics and Microengineering* 17, pp. 1828-1834 (2007).
Monahan et al., "A method for filling complex polymeric microfluidic devices and arrays." *Analytical Chemistry* 73:13 (2001): 3193-3197.
Glazer, Alexander N., "Essentials Extracted, Book Review of Bioconjugate Techniques by Greg T. Hermanson", *Nature* 381 (1996), p. 290.
Gao et al., "Quantum dot-encoded mesoporous beads with high brightness and uniformity: rapid readout using flow cytometry." *Analytical Chemistry* 76:8 (2004): 2406-2410.
Espina et al., Protein microarrays: Molecular profiling technologies for clinical specimens *Proteomics* 3.11 (2003): 2091-2100.
Michalet et al. "Quantum dots for live cells, in vivo imaging, and diagnostics." *Science* 307, pp. 538-544 (2005).
Nielsen et al., "Multiplexed sandwich assays in microarray format." *Journal of Immunological Methods* 290, pp. 107-120 (2004).
Srivastava et al., "Nanotubes light up protein arrays." *Nature Biotechnology* 26:11 (2008), 1244-1246.
Zhou et al., "Constructing the Phase Diagram of an Aqueous Solution of Poly (N-isopropyl acrylamide) by Controlled Microevaporation in a Nanoliter Microchamber." *Macromolecular Rapid Communications* 29, pp. 1363-1367, 2008.
Zhou et al., "Nanoliter dispensing method by degassed poly (dimethylsiloxane) microchannels and its application in protein crystallization." *Analytical Chemistry* 79, 4924-4930 (2007).
Chang, Tse-Wen. "Binding of cells to matrixes of distinct antibodies coated on solid surface." *Journal of immunological Methods* 65, issues 1-2 (1983): 217-223.
Lynge et al., "Polydopamine—a nature-inspired polymer coating for biomedical science." *Nanoscale* 3, pp. 4916-4928 (2011).

(56) References Cited

OTHER PUBLICATIONS

Owens III et al., "Opsonization, biodistribution, and pharmacokinetics of polymeric nanoparticles." *International Journal of Pharmaceutics* 30, pp. 93-102 (2006).
Zhu et al., "Global analysis of protein activities using proteome chips." *Science* 293, pp. 2101-2105 (2001).
Ye et al., "Bioinspired catecholic chemistry for surface modification." *Chemical Society Reviews* 40: 4244-4258 (2011).

\* cited by examiner

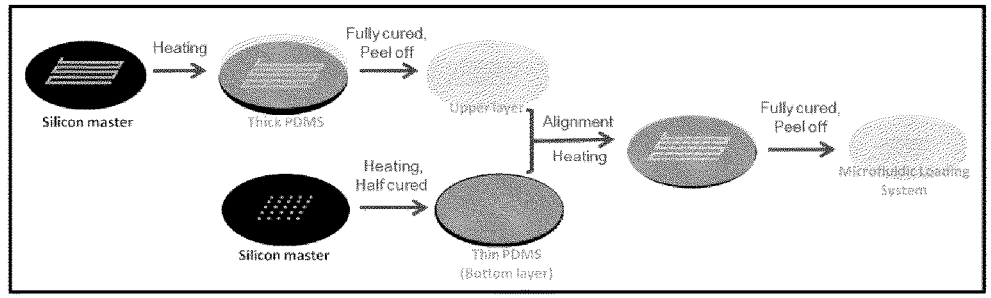

Figure 1. A schematic process of the PDMS microfluidic system fabrication.

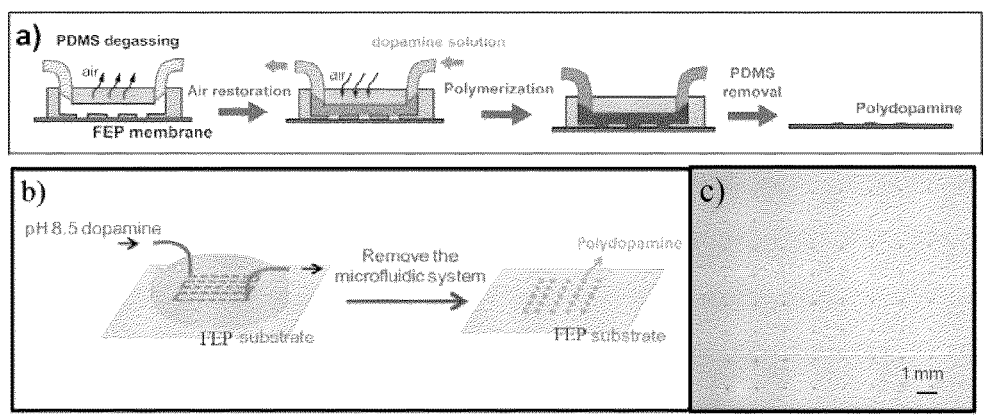

Figure 2. (a) Scheme showing the fabrication method of polydopamine microspots array on the FEP substrate. (b). A schematic process of the formation of an array of polydopamine microspots. (c). A photograph of the polydopamine microspots on the FEP substrate.

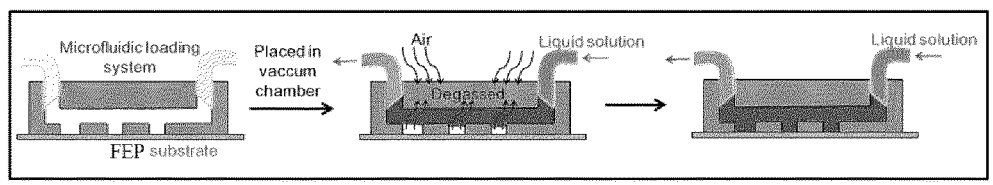

Figure 3. A schematic illustration showing the process of reagent loading with the microfluidic system.

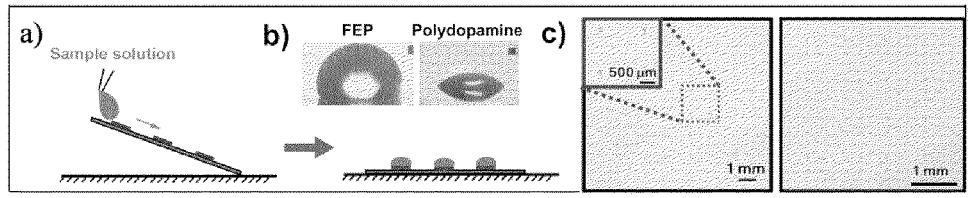

Figure 4. (a) Scheme illustrating the process of droplet formation on the FEP based substrate. (b) Contact angle of the bare FEP substrate (left) and the FEP substrate with polydopamine coated on the surface (right). (c) Bright field image showing the red dye solution dispensed on two different types of polydopamine microarray, 8×8, 200µm in diameter (left) and 4×4×4, 100 µm in diameter (right).

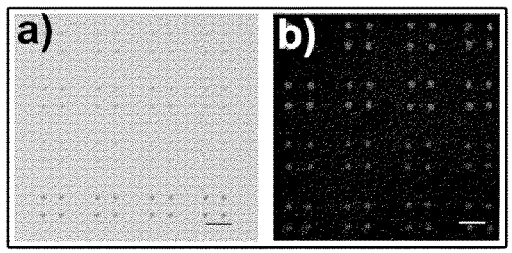

Figure 5. (a) Bright field image showing the dispensing of different dye solution onto the polydopamine microarray. (b) Confocal image showing the conjugation of different fluorescence proteins onto the polydopamine microarray, GFP (green, upper two rows), mCherry (red, bottom two rows). Scale bar: 500 µm.

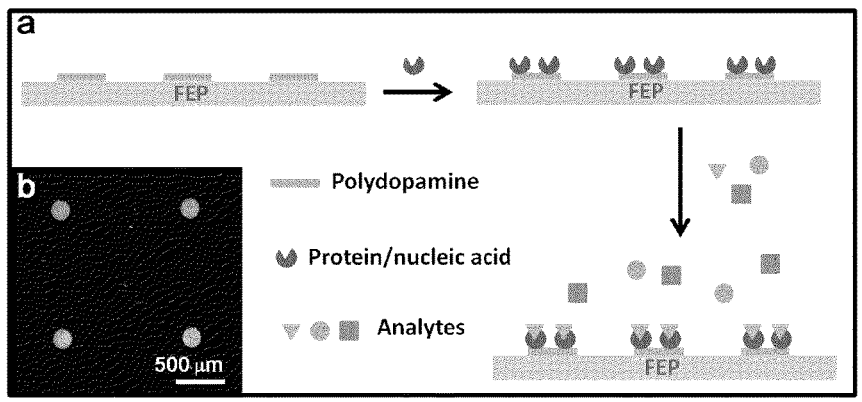

Figure 6. (a). Scheme showing the microarray fabrication and analysis on the polydopamine microspots. (b). Fluorescence image showing the results of using IgG microarray on the fluoropolymer substrate to detect FITC labeled anti-IgG.

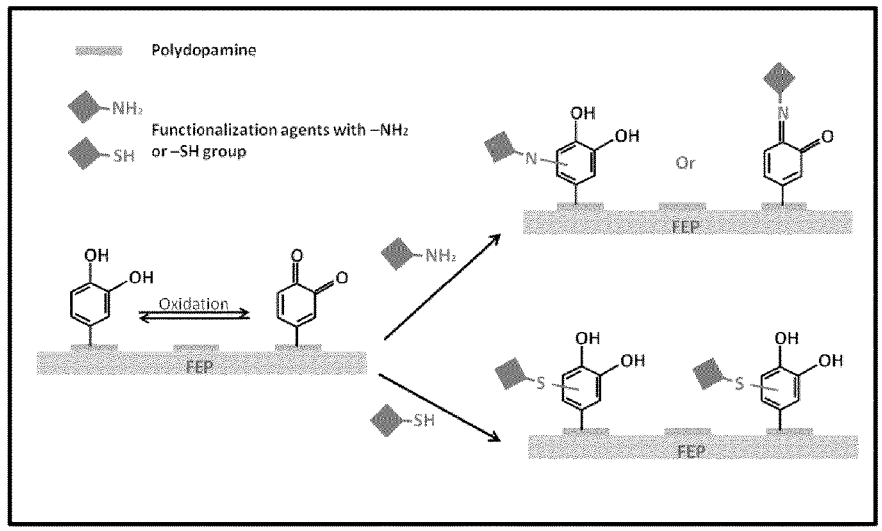

Figure 7. Scheme illustrating the reaction between the polydopamine functional groups and thiol or amine terminated functionalization agents.

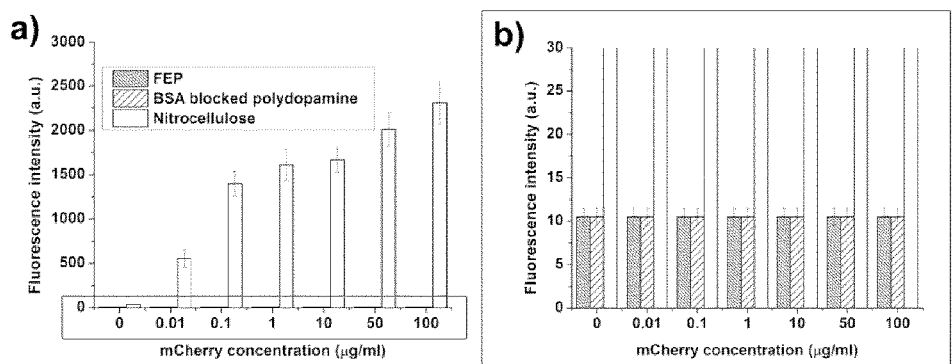

Figure 8. Measurement of the non-specific protein adsorption on different substrates with the red fluorescence protein mCherry. (a) Fluorescence signal intensity change when the substrates were incubated with different concentrations of mCherry. (b) The enlarge plot of the red rectangular portion in (a), showing the signal from either FEP or the BSA blocked polydopamine was undetectable.

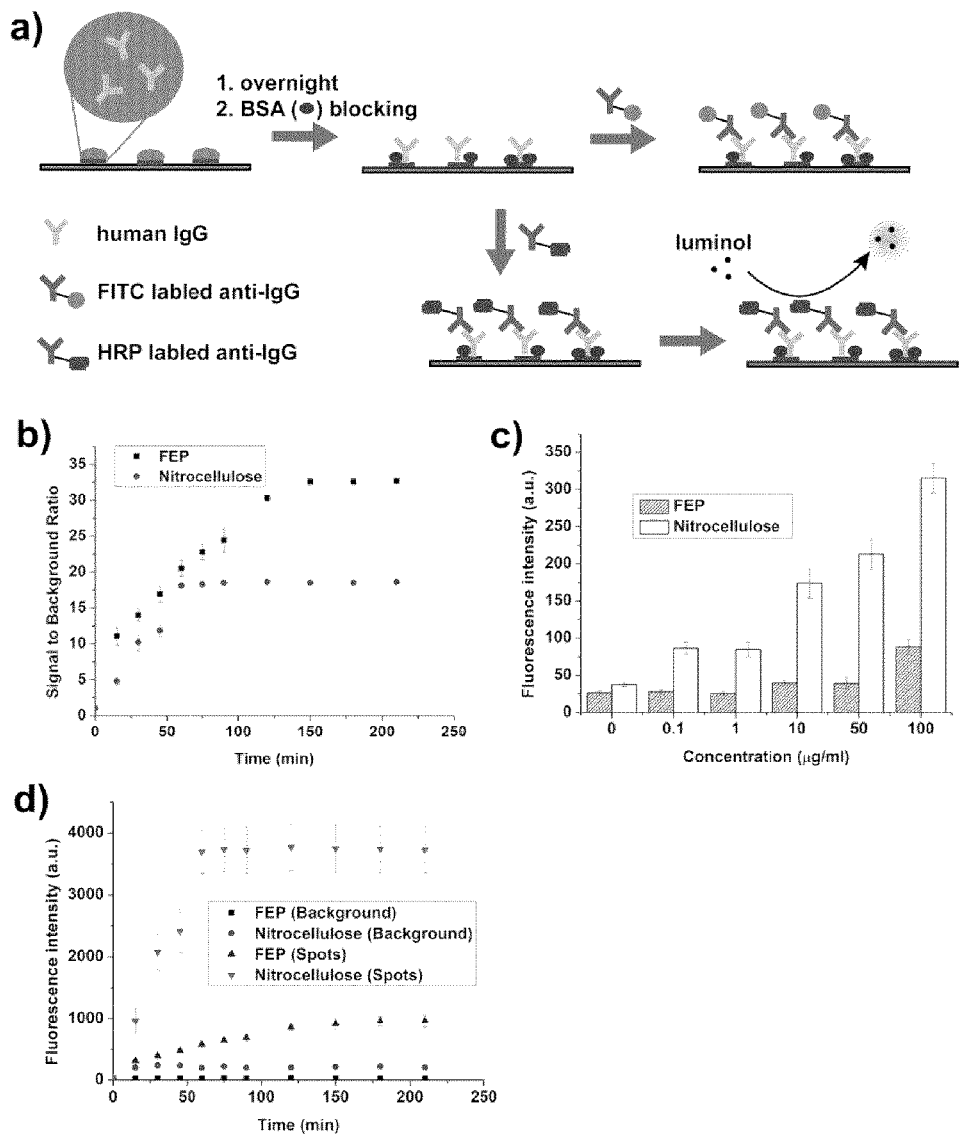

Figure 9 (a) Scheme illustrating the principle of establishing IgG microarray and the fluorescence based and enzyme linked immune chemiluminescence assay for the detection of anti-IgG. (b) The signal-to-background ratio change through time from different substrates. The anti-IgG concentration was 50 µg/ml. (c) Non-specific protein adsorption from different substrates when the substrates were incubated with different concentrations of FITC labeled anti-IgG. (d) The fluorescence signal intensity from the FEP-based substrate and the nitrocellulose substrate for 50 µg/ml FITC labeled anti-IgG.

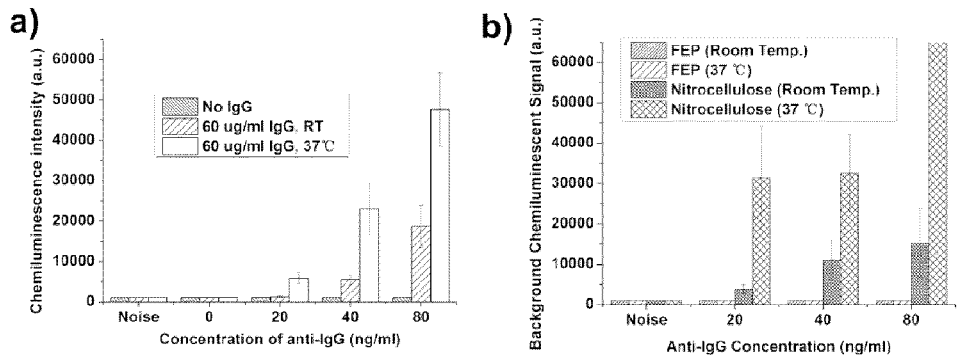

Figure 10. Enzyme linked immune chemiluminescence assay for the detection of the HRP labeled anti-IgG. (a) The optimization of the incubation condition for anti-IgG detection. Target signal intensity increased when the FEP based substrate was incubated under 37 °C. (b) Non-specific protein adsorption from different substrates under different incubation conditions.

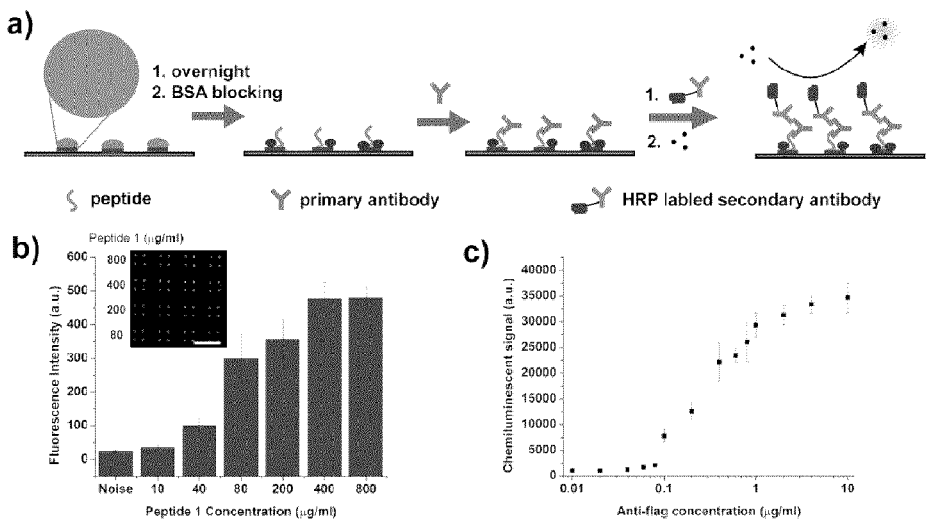

Figure 11. (a) Scheme showing the fabrication of the peptide microarray and the peptide microarray for antibody detection. (b) Optimization of the sampling concentration of peptide 1 onto the polydopamine microspots. Insertion is the confocal image of the peptide microarray with different peptide 1 concentrations. Scale bar: 1 mm. (c) Standard curve for anti-flag antibody detection based on the sflag peptide microarray.

MICROARRAY SUBSTRATE, MICROARRAY, MICROFLUIDIC SYSTEM AND METHODS FOR PREPARING THE SAME

RELATED APPLICATIONS

This application claims priority under 35 U.S.C. § 119(e) to U.S. Provisional Patent Application No. 61/859,896, filed Jul. 30, 2013, the contents of which are incorporated by reference in the entirety.

FIELD OF THE INVENTION

The present application generally relates to a microarray substrate, a microfluidic system and a microarray comprising the substrate, used for detecting, analyzing or studying molecules or particles of interest, particularly biological materials. The present application further relates to a method for preparing the substrate and the microarray, as well as a method for detecting or analyzing molecules of interest in a sample with the microarray comprising the substrate.

BACKGROUND

It is well-known in the art that a series of fluoropolymers, including PTFE (polytetrafluoroethylene), FEP (fluorinated ethylene propylene), PFA (perfluoroalkoxy), etc, have excellent non-sticking property and in general can be used as non-sticking coatings. The PTFE 15 commonly used in non-sticking coatings and is usually referred to as Teflon which is the trademark of the DuPont Company since PTFE was first developed by this company about 70 years ago. Teflon is the brand for a series of synthetic fluoropolymers[1]. Fluoropolymers are known to have no affinity for nearly any materials. Nevertheless, the Messersmith group has demonstrated the affinity of polydopamine to the Teflon materials.[2]

A microarray is a multiplex 2D array on a solid substrate for detecting and analyzing many types of biological materials using high-throughput detection methods. The concept and methodology of microarrays were first introduced and illustrated in antibody microarrays (also referred to as antibody matrix) in 1983 by Chang TW[3] and several patents.[4-6] In early 1990s, Schena and coworkers developed the microarray technology which brought a huge impact to the development of biological analysis techniques. The high-throughput analysis based on microarray technology allowed fast detection of the interactions between biomolecules, and therefore promoted the research in life science and medical diagnosis.[7] Types of microarrays include DNA microarrays, protein microarrays, peptide microarrays or the like.

Protein and peptide microarray is a well developed technique for clinical analysis.[8,9] A typical protein or peptide microarray consists of substrate, functionalized reaction spots, immobilized protein or peptide, target protein and labeled reagents for detection.[10,11] The commonly used labeling reagents are fluorescence molecules,[12,13] horseradish peroxidase (HRP),[14] quantum dots,[15,16] nanoparticles[17] and etc. Based on the labeling reagents, methods such as fluorescence microscopy,[12,17] enzyme linked immunosorbent assay (ELISA) or enzyme linked immune chemiluminescene assay[14,18] have been developed to detect the target protein signal.

The substrate of a microarray, also commonly known as the support, is a material on which the microarray is produced. Nitrocellulose, paper and various silica materials are commonly used substrate for a microarray.[11,19] However, most of these substrates suffer from nonspecific protein adsorption and the adsorption leads to the increase of the background signal and limits the detection.[20] Multi-steps of surface treatment have to be done for nitrocellulose or glass in order to reduce the background signal,[21,22] which significantly increase the substrate cost and the complexity of the substrate handling and storage.

The sensitivity and stability of a protein microarray would be decreased if the substrate surface was not sufficiently blocked. Therefore, different kinds of surface blocking methods have been developed to deactivate the background area, such as polyethylene glycol (PEG),[23] bovine serum albumin (BSA),[24] etc.[25,26,27] These methods usually take a long period to be completely accomplished, and the non-specific protein adsorption is still detectable.[27] Methods of activating and functionalizing the reaction spots on the substrate include adding functional groups of esters, aldehyde-, epoxy-, maleimides, coating polymers which can absorb proteins such as poly-L-lysine, adding amino groups, hydrazines and etC.[11,28] Most of the methods require expensive chemical reagents under strictly controlled conditions, and thus usually require special trained technique and high cost.

Therefore, there exists a need for developing a new substrate for producing microarrays, especially for protein or peptide microarrays.

SUMMARY

In a first aspect, the present application provides a microarray substrate, comprising a piece of fluoropolymer whose surface is modified with polydopamine.

In an embodiment of the present disclosure, the fluoropolymer piece is made of a fluoropolymer material selected from FEP (fluorinated ethylene propylene), PTFE (polytetrafluoroethylene) and PFA (perfluoroalkoxy). Preferably, the fluoropolymer material is FEP.

In an embodiment of the present disclosure, the polydopamine forms an array of microspots on the surface of the fluoropolymer piece. In a preferable embodiment, the polydopamine microspots serve as the reaction sites for microarray analysis, preferably for protein or peptide microarray analysis.

In a second aspect, the present application provides a microarray comprising the microarray substrate disclosed herein. In some embodiments, the microarray further comprises biomolecules, cells and/or micro/nanoparticles which are immobilized on the microarray substrate, preferably on the polydopamine microspots.

Some preferable embodiments of the present disclosure provides a protein or peptide microarray, comprising the microarray substrate disclosed herein, and immobilized proteins or peptides onto the polydopamine, wherein the proteins or peptides form covalent bonding with the polydopamine. Preferably, the proteins or peptides are conjugated onto the polydopamine microspots.

In a third aspect, the present application provides a microfluidic system for delivering chemical and biochemical reagents, which comprises a channel layer, wherein the layer contains microchannels in which a solution can continuously flow. In some embodiments, the channel layer can be made of materials selected from poly(dimethylsiloxane) (PDMS), polystyrene, polycarbonate, glass, and silicon wafers. Preferably, the microfluidic system can be made of PDMS. In some embodiments of the present disclosure, the microfluidic system further comprises a bottom layer which contains an array of micropores and is under the layer containing microchannels.

In a fourth aspect, the present application provides a method for producing microarray substrate disclosed herein, which comprises applying or dispensing a dopamine solution onto a piece of fluoropolymer. In an embodiment, the dispensing comprises binding a microfluidic system with a piece of fluoropolymer, and keeping the dopamine solution flowing over the surface of the fluoropolymer which is exposed to the dopamine solution through the micropores of the microfluidic system, thereby forming an array of polydopamine microspots on the surface of the fluoropolymer piece after removal of the microfluidic system.

In a fifth aspect, the present application provides a method for preparing a microarray, which comprises dispensing a reagent of interest onto the surface of the microarray substrate disclosed herein. In embodiments of the present disclosure, the reagent may be selected from proteins, peptides, nucleic acids, oligonucleotides, cells and/or micro/nanoparticles, and the microarray accordingly can be used to detect or analyze proteins, peptides, nucleic acids, cells or micro/nanoparticles.

Some preferable embodiments of the present disclosure provides a method for preparing a protein or peptide microarray, which comprises dispensing a protein or peptide solution onto the microarray substrate disclosed herein and incubating the protein or peptide solution on the substrate surface, wherein the protein or peptide forms covalent bonding with the polydopamine and is preferably conjugated onto the polydopamine microspots.

In a sixth aspect, the present application provides a method for detecting a substance of interest in a sample using the microarray disclosed herein, which comprises dispensing the sample on the microarray and detecting the binding of the substance with the microarray, particularly with the reagent pre-dispensed onto the microarray substrate disclosed herein. In other embodiments of the method, the binding can be detected via colorimetry, fluorescence, luminescence, electrochemical signals, mass spectrometry, or radioactivity signals and so on, which are associated with the binding events.

In other aspects, the present application provides a process of making microfluidic systems, for example using photolithography[29] or soft lithography method.[30] Other embodiments of the present disclosure relate to use of the microarray or the microarray substrate for detection, analysis, and study of a substance of interest.

BRIEF DESCRIPTION OF THE DRAWINGS

FIG. 1 shows a schematic process of the PDMS microfluidic system fabrication.

FIG. 2 (a) is a scheme showing the fabrication method of polydopamine microspots array on the FEP substrate; FIG. 2(b) illustrates the formation of an array of polydopamine microspots, and FIG. 2(c) shows a photograph of the polydopamine microspots on a piece of fluoropolymer.

FIG. 3 is a schematic illustration showing the process of reagent loading with a microfluidic system.

FIG. 4(a) shows a scheme illustrating the process of droplet formation on microspots; FIG. 4(b) shows contact angles of the bare FEP substrate (left) and the FEP substrate with polydopamine coated on the surface (right); and FIG. 4(c) are bright field images showing the red dye solution dispensed on two different types of polydopamine microarray, 8×8, 200 μm in diameter (left) and 4×4×4, 100 μm in diameter (right).

FIG. 5 (a) is a bright field image showing the dispensing of different dye solutions onto the polydopamine microarray; and FIG. 5 (b) is a confocal image showing the conjugation of different fluorescence proteins onto the polydopamine microarray, GFP (green, upper two rows), mCherry (red, bottom two rows). Scale bar: 500 μm.

FIG. 6(a) shows a scheme of the microarray fabrication and analysis on the polydopamine microspots, and FIG. 6(b) is a fluorescence image showing the results of using IgG microarray on the fluoropolymer substrate to detect FITC labeled anti-IgG.

FIG. 7 shows a scheme illustrating the reaction between the polydopamine functional groups and thiol or amine terminated functionalization agents.

FIG. 8 shows measurements of the non-specific protein adsorption on different substrates with the red fluorescence protein mCherry. (a) Fluorescence signal intensity change when the substrates were incubated with different concentrations of mCherry. (b) The enlarge picture of the red square in (a), showing the signal from either FEP or the BSA blocked polydopamine was undetectable.

FIG. 9(a) shows a scheme illustrating the principle of establishing IgG microarray and the fluorescence based and enzyme linked immune chemiluminescence assay for the detection of anti-IgG. FIG. 9 (b) shows the signal-to-background ratio change through time from different substrates. The anti-IgG concentration was 50 μg/ml. FIG. 9 (c) shows non-specific protein adsorption from different substrates when the substrates were incubated with different concentrations of FITC labeled anti-IgG. FIG. 9 (d) shows the fluorescence signal intensity change through time from the FEP based substrate and the nitrocellulose substrate for 50 μg/ml FITC labeled anti-IgG.

FIG. 10 shows enzyme-linked immune chemiluminescence assay for the detection of the HRP labeled anti-IgG. (a) illustrates the optimization of the incubation condition for anti-IgG detection. Target signal intensity increased when the Teflon based substrate was incubated under 37° C. (b) illustrates non-specific protein adsorption from different substrates under different incubation conditions.

FIG. 11(a) is a scheme showing the fabrication of the peptide microarray and the peptide microarray for antibody detection. FIG. 11(b) illustrates optimization of the sampling concentration of peptide 1 onto the polydopamine microspots. Insertion is the confocal image of the peptide microarray with different peptide 1 concentrations. Scale bar: 1 mm. FIG. 11(c) is a standard curve for anti-flag antibody detection based on the sflag peptide microarray.

DEFINITIONS

As used herein, the term "microarray" is characterized by high density of array of small spots. The microarray comprises a specific support and biological materials on the support, in which the biological materials form an array appropriated for high throughput detection of one or more test substances. The microarray typically includes nucleic acid microarrays, protein microarrays, peptide microarrays or the like, which can be used to detect various molecules of interest.

As disclosed herein, the substrate of the present disclosure comprises polydopamine, fluoropolymer, and optionally a support material. The polydopamine is configured on the surface of the fluoropolymer. Where the support material is comprised, the fluoropolymer is applied on top of the support material surface. The support material may include, but not limited to plastic, glass wafers or other inert materials.

As used herein, the term "fluoropolymer" is a fluorocarbon based polymer with multiple strong carbon-fluorine bonds. It is characterized by a high resistance to solvents, acids, and bases. Fluoropolymers have excellent non-sticking and friction reducing properties. Also, fluoropolymer is chemically stable due to the multiple carbon-fluorine bonds. Fluoropolymers may be mechanically characterized as thermosets or thermoplastics. Fluoropolymers can be homopolymers or copolymers.

As used herein, the terms "PTFE" and "polytetrafluoroethylene" is a synthetic fluoropolymer of tetrafluoroethylene that has numerous applications. The best known brand name of PTFE is Teflon by DuPont Co. As used herein, the term "FEP" is a synthetic fluoropolymer named "fluorinated ethylene propylene". FEP is a copolymer of hexafluoropropylene and tetrafluoroethylene. FEP was invented by DuPont with the brand name of Teflon FEP.

As used herein, the term "fluoropolymer chip" refers to a carrier having polydopamine configured or dispensed on the surface of the fluoropolymer, in which the chip can be used to prepare a microarray for high-throughput detection of a test substance.

As used herein, the terms "fluoropolymer chip" and "fluoropolymer substrate" are used interchangeably in the context of the disclosure.

Reference throughout this specification to "one embodiment", or "an embodiment", or "another embodiment", or "a still another embodiment", "embodiments" or "the embodiment" means that a particular referent feature, structure, or characteristic described in connection with the embodiment(s) is included in at least one embodiment. Thus, the appearance of the phrases "one embodiment", or "an embodiment", or "another embodiment", or "embodiments" in various places throughout this specification are not necessarily all referring to the same embodiment. Furthermore, the particular features, structures, or characteristics may be combined in any suitable manner in one or more embodiments.

In addition, reference to an element by the indefinite article "a" or "an" does not exclude the possibility that more than one of the element is present, unless the context clearly requires that there be one and only one of the elements. The indefinite article "a" or "an" thus usually means "at least one".

DETAILED DESCRIPTION OF THE PREFERRED EMBODIMENTS

It is well-known in the art that various fluoropolymers have a non-sticking property. Such materials have not been used as the substrate of a microarray up to now. In the present disclosure, the inventors for the first time develop a fluoropolymer chip or fluoropolymer substrate to provide a new means in the technical field of micro array.

In a first aspect, a microarray substrate is provided, which comprises a piece of fluoropolymer whose surface is modified with polydopamine.

An embodiment of the present disclosure provides a microarray substrate for analysis of a substance of interest, comprising a piece of fluoropolymer and polydopamine, wherein the polydopamine can form an array of microspots on the surface of the fluoropolymer piece and is used for attaching a reagent for analyzing or detecting the substance of interest.

In an embodiment of the present disclosure, the fluoropolymer piece can be made of a fluoropolymer material selected from FEP (fluorinated ethylene propylene), PTFE (polytetrafluoroethylene) and PFA (perfluoroalkoxy). In a preferable embodiment, the fluoropolymer material is FEP.

In other embodiments, the polydopamine may be modified by a functionalization agent containing thiol or amino groups. In an embodiment, the functionalization agent may be selected from the group consisting of thioglycolic acid, cysteine, mercaptoethylamine, mercaptoethanol and other regents comprising thiol groups, as well as p-aminophenol, aminosalicylic acid, aminobenzoic acid, various amino acids and other regents comprising amino groups. In a preferable embodiment, the functionalization agent can be covalently bound to the polydopamine. In some embodiments, the polydopamine allows immobilization of proteins, peptides, nucleic acids, oligonucleotides, cells, polymers, small probe molecules or micro/nanoparticles. The nucleic acids are preferably DNA or RNA.

Optionally, microarray substrate disclosed herein further comprises a support material which is underneath the fluoropolymer piece. In an embodiment, the support material may be glass or plastic or other inert materials.

In a second aspect, the present application provides a microarray comprising the microarray substrate disclosed herein. In some embodiments, the microarray further comprises biomolecules, cells and/or micro/nanoparticles which are immobilized on the microarray substrate, preferably on the polydopamine microspots. In an embodiment, the biomolecules can be proteins, peptides, nucleic acids, oligonucleotides, polymers, or small probe molecules.

In an embodiment, the microarray comprise cells which are attached to the polydopamine microspots, and thus can be used for performing tissue engineering, stem cell differentiation or cell targeted drug efficacy testing.

In another embodiment, micro/nanoparticles immobilized on the microarray substrate can be modified with a thiol or amino group and conjugated onto the polydopamine microspots. Thus, the microarray comprising micro/nanoparticles can be used for surface patterning and for performing detection of biomolecules such as by enzyme assay or self-assembled monolayer studies.

Still in another embodiment, the nucleic acids comprising DNA and RNA, or oligonucleotides are modified with a thiol or amino group at either or both of their ends, and thus can bind onto the polydopamine microspots to generate corresponding micro array.

Some preferable embodiments of the present application provides a protein or peptide microarray, comprising the microarray substrate disclosed herein, and immobilized proteins or peptides onto the polydopamine, wherein the proteins or peptides form covalent bonding with the polydopamine. Preferably, the proteins or peptides can be directly conjugated to the polydopamine through covalent bonding and electrostatic adsorption.

The inventors have successfully fabricated protein or peptide microarray on the substrate disclosed herein for protein analysis. No complicated surface modification is needed either to activate the microspots or deactivate the background area. The nonspecific protein adsorption on the background area of the substrate has been significantly decreased in a protein or peptide microarray disclosed herein. The target signals from different pieces of substrates have good repeatability and can guarantee the stability of using the microarray substrate for more complicated analysis systems.

In a third aspect, a microfluidic system for delivering chemical and biochemical reagents is provided, which comprises a channel layer, wherein the layer contains microchannels in which a solution can continuously flow. In some embodiments, the channel layer can be made of materials selected from poly(dimethylsiloxane) (PDMS), polystyrene, polycarbonate, glass, and silicon wafers. Preferably, the microfluidic system is made of PDMS. In some embodiments of the present disclosure, the microfluidic system further comprises a bottom layer which contains an array of micropores and is under the layer containing microchannels.

In an embodiment, the microfluidic system is a two-layer microfluidic chip, in which the upper layer is a channel layer, and the bottom is a membrane with micropore array. The chip is fabricated by photolithography and soft lithography, and the bonding of the two layers is through thermo controlling.[31] In another embodiment, the upper and bottom layers are made of various materials such as poly(dimethylsiloxane) (PDMS), polystyrene, polycarbonate, glass, and silicon wafers.

In a fourth aspect, the present application provides a method for producing microarray substrate disclosed herein, which comprises applying or dispensing a dopamine solution onto a piece of fluoropolymer, such as FEP (fluorinated ethylene propylene), PTFE (polytetrafluoroethylene) and PFA (perfluoroalkoxy).

In an embodiment, the dispensing comprises binding a microfluidic system disclosed herein with a piece of fluoropolymer, and keeping the dopamine solution flowing over the surface of the fluoropolymer which is exposed to the dopamine solution through the micropores of the microfluidic system, thereby forming an array of polydopamine microspots on the surface of the fluoropolymer piece after removal of the microfluidic system. In an embodiment of the method, the size of the micropores determines the size of the microspots.

In a fifth aspect, the present application provides a method for preparing a microarray, which comprises dispensing a reagent of interest onto the surface of the microarray substrate disclosed herein. In embodiments of the present disclosure, the reagent may be selected from proteins, peptides, nucleic acids, oligonucleotides, cells and/or micro/nanoparticles, and the microarray accordingly can be used to detect or analyze proteins, peptides, nucleic acids, cells or micro/nanoparticles.

In some embodiments, the method for preparing a microarray comprises rolling a droplet of a reagent of interest on the surface of the substrate, wherein the reagent can be captured by polydopamine microspots, and thereby forms an array on the substrate surface. In other embodiments, the method for preparing a microarray comprises placing a microfluidic system disclosed herein above the substrate surface, wherein the reagent is introduced into the channels of the microfluidic system and flows over the microspots of the substrate. After removal of the microfluidic system, only the microspots will be covered by the reagent.

Some preferable embodiments of the present disclosure provides a method for preparing a protein or peptide microarray, which comprises dispensing a protein or peptide solution onto the microarray substrate disclosed herein and incubating the protein or peptide solution on the substrate surface for a period of time, for example, several hours, wherein the protein or peptide forms covalent bonding with the polydopamine and is preferably conjugated onto the polydopamine microspots.

The microarray substrate and the protein or peptide microarray thus prepared have at least one of the following advantages: 1) no complicated surface modification is needed; 2) cost-saving and time-saving; 3) low background signal; 4) high sensitivity of detection; 5) good repeatability of target signals; and so on.

In a sixth aspect, the present application provides a method for detecting a substance of interest in a sample using the microarray disclosed herein, which comprises dispensing the sample on the microarray and detecting the binding of the substance with the microarray, particularly with the reagent pre-dispensed onto the microarray substrate. In other embodiments of the method, the binding can be detected via colorimetry, fluorescence, luminescence, electrochemical signals, mass spectrometry, or radioactivity signals, which are associated with the binding events.

In other aspects, the present application provides a method for preparing a microfluidic system disclosed herein. The microfluidic loading system can be used to dispense polydopamine solution on the fluoropolymer piece, or to dispense a sample solution comprising a reagent of interest onto the fluoropolymer substrate surface.

Other particular embodiments of the present disclosure are described as follows.

Fabrication of the Multilayer Microfluidic Loading Device

A multilayer microfluidic loading device was fabricated to make the polydopamine microspots onto the fluoropolymer membrane. The microfluidic system can also be used to deliver chemical and biochemical reagents to the fluoropolymer substrate as disclosed below. The terms "microfluidic system" and "microfluidic loading device" are used interchangeably in the context of the disclosure.

The microfluidic system can be fabricated using various materials, such as poly(dimethylsiloxane) (PDMS), polystyrene, polycarbonate, glass, and silicon wafers. For example, the system was made of PDMS, a commonly used material for microfluidic chips.[29] PDMS is known to be permeable of gas and water.[32] As an example, a process of making microfluidic systems comprises using photolithography and soft lithography method.[30]

In one embodiment, a microfluidic system comprises or is composed of two layers with different patterns. Taking the PDMS microfluidic system for an example, the upper PDMS layer is a channel layer and is fabricated by casting the PDMS precursor, such as a mixture of liquid siloxane monomer and the curing agent, against a silicon master. The silicon master is produced using photolithography.[29] The silicon master acts as a mold and contains relief structure complementary to the micro patterns (microchannels herein) (FIG. 1). The bottom PDMS layer is a thin PDMS membrane with micropore array. This thin PDMS membrane is fabricated by spin-coating a thin layer of the PDMS precursor containing a lower percentage of the curing agent onto the surface of a second silicon master. The second silicon master contains arrays of microspots. In most cases, the size of the microspos is about 100-500 µm in diameter, preferably about 200 µm. The size of the microspots determines the size of the micropores of the PDMS membrane.

In some embodiments, the bonding of the two layers of the microfluidic system is through thermo controlling.[31] Particularly, the bonding of the two layers is achieved by controlling different curing rates between the upper and bottom layers. Taking the PDMS microfluidic system as an example, the two PDMS layers have different chemical compositions, and therefore it is easy to control the upper layer being totally cured while the bottom layer being half-cured under the same thermal treatment condition. The upper layer will be aligned with the bottom layer. After another few hours of thermal treatment, the two layers could be fully bonded (FIG. 1).

Fabricating Polydopamine Microspots on Fluoropolymer

In embodiments of the present disclosure, polydopamine is used to modify the fluoropolymer (such as PTFE (polytetrafluoroethylene), FEP (fluorinated ethylene propylene) and PFA (perfluoroalkoxy)) surface to allow immobilization of proteins, peptides, nucleic acids, polymers, small probe molecules, cells or other entities of interest. In one embodiment of the disclosure, in order to fabricate a thin polydopamine layer on the surface of the fluoropolymer, the continuous flowing of the fresh dopamine solution (such as in basic solution, about 1-10 g/L in concentration) is needed. For the purpose of creating a continuous flow over the determined locations of the surface of the fluoropolymer, in one embodiment of the present disclosure, a microfluidic loading system is employed. Underneath the micropores of the microfluidic system, the fluoropolymer surface is exposed to the flow of the dopamine solution.

In a still embodiment, the surface of the fluoropolymer, such as PTFE (polytetrafluoroethylene), FEP (fluorinated ethylene propylene) and PFA (perfluoroalkoxy) substrates, is cleaned by detergent, alcohol and pure water with sonication, respectively. The microfluidic system will be bound tightly with the piece of fluoropolymer, e.g., by clamps.

In other embodiment, vacuum is applied in process of the microfluidic system as well as preparation of polydopamine layer on the surface of the fluoropolymer.[33] For example, due to the gas permeability of PDMS, vacuum is generated in pre-degassed PDMS, and the whole microchannels and micropores are filled with dopamine solution with no air bubbles trapped inside (FIG. 2a).

During the dopamine polymerization process, the microfluidic system will be connected to a reservoir containing the dopamine solution, and the dopamine solution will keep flowing driven by a peristaltic pump. After a few hours, a thin layer of polydopamine will be formed both on the microchannel walls and on the surface of the fluoropolymer which is exposed to the dopamine solution through the micropores. After removing the microfluidic system, arrays of microspots which present thin polydopamine layer on the fluoropolymer will be generated (FIG. 2b,c).

In other embodiments, the fluoropolymer piece disclosed herein can be a slab of fluoropolymer, or a thin layer of fluoropolymer on top of a plastic, glass wafer, or other inert materials.

Dispensing Reagents onto the Microspots

In embodiments of the present disclosure, chemical or biochemical reagents are dispensed on the polydopamine microspots on the surface of the fluoropolymer, such as PTFE (polytetrafluoroethylene), FEP (fluorinated ethylene propylene) and PFA (perfluoroalkoxy), to produce microarrays for analysis or diagnosis or other use disclosed herein. Herein we use "fluoropolymer chip" to refer to the fluoropolymer piece with the microspots on its surface.

In an embodiment, dispensing small quantity sample solution on the fluoropolymer chip (such as PTFE (polytetrafluoroethylene), FEP (fluorinated ethylene propylene) and PFA (perfluoroalkoxy) chips) can be done by rolling a droplet of the sample solution on the surface of the fluoropolymer chip. The rolling of the droplet is achieved by tilting the fluoropolymer chip surface or by mechanical force. Liquid solution can be quickly captured by the hydrophilic polydopamine microspots and form an array of droplets on the fluoropolymer chip surface (FIG. 4). In some embodiments, different sample solutions could be introduced onto the specified microspots in this way to form a multi functionalized array.

In an embodiment, dispensing small quantity of sample solution on the fluoropolymer chip can also be done by placing a microfluidic system, containing microchannels above the microspots. In an embodiment, the microfluidic system can be of single layer, containing only the channels. Alternatively, the microfluidic system can have the same configuration as the one for dispensing dopamine solution, which contains a layer of microchannels plus a layer of micropores. Liquid sample solution can be introduced into the microchannels and flow over the polydopamine microspots of the fluoropolymer chip (FIG. 3). After the removal of the microfluidic system, only the microspots will be covered by the sample solution.

In other embodiments, for generating protein microarrays, proteins can be directly conjugated to polydopamine through covalent bonding and electrostatic adsorption. Protein microarray can be formed by dispensing the protein solution onto the polydopamine microspots and incubating for several hours. In still other embodiments, DNA, RNA and oligonucleotides with the end being modified by thiols or amines can also bind onto the polydopamine microspots to generate the corresponding microarray (FIG. 6).[34]

Submicroliter Biochemical Reactions in the Droplets on the Microspots

In embodiments of the present disclosure, biochemical reactions such as polymerase chain reaction (PCR) can be done on the fluoropolymer chip disclosed herein. Microspots with femtoliter to nanoliter liquid droplets can be fabricated. Sample solution can be fast dispensed onto each microspot and form a droplet. In embodiments of the present disclosure, with the protection of fluorinated oil to prevent the solution evaporation, a large number of reactions can be done on the fluoropolymer chip in parallel. In other embodiment, the array of droplets on the fluoropolymer chip disclosed herein can be used for digital PCR.[35]

Modifying Surface Property of the Microspots

In embodiments of the present disclosure, various chemical function groups can be introduced onto the polydopamine microspots, as illustrated in FIG. 7. The functionalization agent contains either thiol or amine groups and can be covalently bound to the polydopamine.[34] Studies have also shown successful conjugation of biomolecules containing amine and thiol groups onto the polydopamine.[35,36,37] In an embodiment of the present disclosure, the functionalization agent can be selected from the group consisting of thioglycollic acid, cysteine, mercaptoethylamine, mercaptoethanoland and other regents comprising thiol groups, as well as p-aminophenol, aminosalicylic acid, aminobenzoic acid, various amino acids and other regents comprising amino groups.

Depositing Cells or Particles onto the Microspots

In other embodiments, suspension of cells can be directly dispensed onto the polydopamine microspots on the fluoropolymer chip disclosed herein. The deposition of the cells allows several kinds of researches to be performed, such as tissue engineering, stem cell differentiation, cell targeted drug efficacy testing, and etc. Single cell analysis is also possible by depositing single cells onto the microspots. In other embodiments, micro/nanoparticles suspended in solutions could also be dispensed onto the microspots. The patterned micro or nanoparticles can be used in applications such as ultra-sensitive detection of biomolecules. If the particles have been modified with reactive thiols or amines, the particles will be able to be conjugated onto the microspots for further applications such as enzyme assay, self-assembled monolayer studies, etc.

Comparison with Existing or Previous Product

The fabricating protein microarray using the fluoropolymer chip disclosed herein may have at least one of the following advantages compared with the existing products.

The cost of the fabricating protein microarray using the fluoropolymer chip disclosed herein is lower than existing products. Unlike glass and nitrocellulose, fluoropolymer chip disclosed herein may not need further modification during the fabrication process.

The sensitivity of the microarray using the fluoropolymer chip disclosed herein is better than existing product. Compared with the surface modified glass and nitrocellulose, the fluoropolymer disclosed herein has superior protein-repelling and anti-fouling surface property. Consequently, the background signal of the fluoropolymer chip disclosed herein, especially FEP chip, is reduced, which improves the sensitivity.

EXAMPLES

Example 1: Fabrication of PDMS Microfluidic Loading Device

PDMS microfluidic device composed of two layers, was fabricated using Siloxane Sylgard® 184 Silicone Elastomer Kit (Dow Corning) by soft lithography method. The Kit comprised PDMS precursor and curing agents.

The upper PDMS layer was fabricated by casting the PDMS precursor, a mixture of liquid siloxane monomer (Sylgard® 184, Dow Corning) and the curing agent (5:1), against a silicon master. The silicon master was patterned using photolithography. The silicon master acted as a mold and contained relief structure complementary to the micro patterns (microchannels herein) (FIG. 1).

The bottom PDMS layer was a thin PDMS membrane (about 20 µm in thickness) containing micropores. The bottom layer was fabricated by spin-coating a thin layer of the PDMS precursor (siloxane monomer: curing agent=20:1) onto the surface of a second silicon master. The silicon master contained arrays of microspots with the size of 200 µm in diameter. The size of the microspots determined the size of the micropores of the PDMS membrane. Hundreds to thousands of micropores could easily fit in one 1 cm×1 cm PDMS membrane.

The bonding of the two PDMS layers was achieved by controlling the different curing rate between the upper and bottom PDMS layers. Due to the different composition of the two layers, after 30 min thermo annealing at 80° C., the upper layer was totally cured while the bottom layer was half-cured. The upper layer was peeled off from the silicon master, and the alignment of the two layers was performed. After around 2 to 5 hours of thermal annealing, the two layers were fully bound (FIG. 1), and thus the PDMS microfluidic device was prepared.

Example 2: Fabricating Polydopamine Microspots on a Piece of Fluoropolymer

Dopamine used in this example was purchased from Sigma-aldrich, and FEP (20 µm) was from Shanghai Yuyisong Plastic Products Co., Ltd.

A fresh dopamine solution (pH 8.5, 2 g/L) was prepared. A piece of FEP of 1 cm×1 cm was first cleaned by surfactant, ethanol and distilled water three times with ultra sonic.

The PDMS microfluidic system as prepared in Example 1 was bound tightly with the FEP piece by clamps and degassed in a vacuum desiccator for 30 min (FIG. 2a). Once the degassing step was finished, fresh dopamine solution (pH=8.5) was introduced into the system. The solution filled the upper channel layer without delay, and then gradually filled the empty space in the micropores in the bottom layer. The degassed PDMS microfluidic system gas accelerated the filling process by adsorbing the air in the microchannel and micropores. Underneath the micropores, the FEP surface was exposed to the flow of the dopamine solution.

The whole process was finished within 5 min. Followed by the solution loading and bubble exclusion, the fresh dopamine solution was continuously supplied into the assembly for 3 hours. During the period, the solution would turn from transparent and colorless into dark brown, indicating the formation of polydopamine coating. After the removal of the microfluidic device from the FEP piece, an array of polydopamine microspots (each had the size of 200 µm in diameter) which presented a thin polydopamine layer on the FEP was generated (FIG. 2). Hundreds to thousands of microspots were generated in one 1 cm×1 cm FEP piece, with the original geometry of the micropore array.

Example 3: Dispensing Reagents onto the Microspots

Chemical or biochemical reagents were dispensed on the microspots on the FEP substrate to produce microarrays for analysis or diagnosis or other use disclosed herein.

Liquid solutions could be dispensed onto the microspots by directly flowing over the substrate surface (FIG. 4) or by means of a PDMS microfluidic system (FIG. 3). Particularly, the following two methods were used for dispensing small quantity sample solution on the FEP chip.

The fast dispensing could be done by rolling a droplet of the sample solution on the surface of the fluoropolymer chip. The rolling of the droplet was achieved by tilting the FEP chip surface or by mechanical force. Due to the hydrophilicity difference of polydopamine and FEP, liquid solutions were trapped only on the polydopamine microspots (FIG. 4). As shown in FIG. 4c, the amount of liquid solutions was evenly distributed on each microspots, which facilitated the robust performance of the microarray.

The dispensing could also be done by placing a PDMS microfluidic system as prepared in Example 1 above the microspots. Liquid sample solution was introduced into the channels and flow over the microspots of the FEP substrate. After the removal of the PDMS microfluidic system, only the microspots were covered by the sample solution (FIG. 3).

Different sample solutions could also be introduced onto the specified microspots to form a multi-functionalized array utilizing a PDMS microfluidic system (FIG. 5a). A microfluidic chip with channels was used to help achieve the multi-solution dispensing. The channels were aligned with the microspots, and the microfluidic chip was then boned with the FEP chip. By connecting the system with a syringe, sample solutions were first injected into the channels and then pulled out. Due to the hydrophilicity difference of polydopamine and FEP, liquid solutions were trapped only on the polydopamine microspots. As shown in FIG. 5a, the amount of liquid solutions was evenly distributed on each microspots, which facilitated the robust performance of the microarray.

Example 4: Detection of Anti-Antibody with Protein Microarrays

The human IgG protein (Beijing Dingguo Changsheng Biotechnology Co., Ltd.) was directly conjugated to polydopamine microspots through covalent bonding and electrostatic adsorption. The protein microarray was formed by dispensing the IgG solution (1 mg/ml) onto the FEP substrate prepared in Example 2 and incubating overnight at 4° C. FITC labeled anti-IgG solution (50 µg/ml) (Beijing Dingguo Changsheng Biotechnology Co., Ltd.) was dispensed to contact with IgG conjugated to the polydopamine microspots on the microarray. The dispensing of the IgG and anti-IgG was conducted using the droplet rolling method described in Example 3. As shown in FIG. 6(b), the result of using IgG microarray on the FEP substrate to detect FITC labeled anti-IgG was shown in fluorescence image (green).

Example 5: Fluorescence Based Protein Microarray Analysis

To form the protein microarray on the substrate, protein solutions were dispensed onto the microspots and incubated at 4° C. overnight. The amine and thiol groups on the protein would form covalent bonding with the quinone or catechol groups on the polydopamine, and therefore functionalize the microspots. The self extracted green fluorescence protein (GFP) (~0.5 mg/ml) and red fluorescence protein (mCherry) (~0.5 mg/ml) were used to test the conjugation efficiency of proteins on the polydopamine spots (FIG. 5b). From the results, only the microspots showed green or red fluorescence, and the fluorescence intensity on the microspot showed little fluctuation, which indicating the even distribution of the proteins on the each microspot. The fluorescence intensity from different microspots with the same sample was consistent, which demonstrated a good repeatability in the experiment. The fluorescence intensity was detected using Laser Scanning Confocal Microscope (Nikon).

We then fabricated a human IgG based protein microarray, and used the FITC labeled rabbit anti-human secondary antibody (Beijing Dingguo Changsheng Biotechnology Co., Ltd.) to test the non-specific protein adsorption on the FEP (FIGS. 8 and 9). Briefly, 60 µg/ml human IgG (Beijing Dingguo Changsheng Biotechnology Co., Ltd.) solution was deposited onto the microspots using the droplet rolling method described in Example 3 and incubated at 4° C. overnight. 5 mg/ml BSA (Beijing Dingguo Changsheng Biotechnology Co., Ltd.) solution was then used to block the polydopamine microspots for 1 hour. The whole substrate was then exposed to the secondary antibody solution, and incubated at room temperature with continues shaking for 3 hours. Different concentrations of the secondary antibody solution were used to see the fluorescence signal change of both the microspots and the background (FIG. 9c). The red fluorescence protein having no specific interaction with the human IgG was used as a negative control (FIG. 8). Nitrocellulose (Whatman) was used to compare the protein adsorption with the invented substrate. For nitrocellulose, the BSA blocking was performed overnight to make sure the nonspecific protein adsorption on the material was reduced to minimum.

The background signal of the FEP based substrate was similar as the noise of the instrument for both FITC labeled secondary antibody and mCherry. By contrast, nitrocellulose suffered from the nonspecific protein adsorption problem in both cases (FIG. 8, FIG. 9c). Although the target fluorescence signal intensity from both polydopamine microspots and nitrocellulose increased with the increase of the secondary antibody concentration, the signal-to-background ratio demonstrated the better performance of FEP based substrate (FIG. 9b).

Example 6: Enzyme Linked Immune Chemiluminescence Assay Based on the Substrate Unlike the fluorescence based microarray, the enzyme linked immune chemiluminescence assay used HRP induced chemiluminescence to amplify the target signal and thus increased the detection limitation. Herein, the human IgG microarray was used as a simple model, and the HRP labeled goat anti human secondary antibody (Beijing Dingguo Changsheng Biotechnology Co., Ltd.) was used along with the $H_2O_2$ to induce the chemiluminescence from luminol (FIG. 9a). SuperSignal® ELISA Femto Maximum Sensitivity Substrate Kit (Thermo) was used in this experiment.

After sampling and surface blocking, the substrate with protein microarray was incubated with different concentrations of HRP labeled secondary antibody. The experiment was performed at room temperature or 37° C. for 30 min. After incubation, the substrate was washed thoroughly with 0.02% Tween buffer. $H_2O_2$ and luminol solution was then applied onto the substrate. The chemiluminescent signal was detected by GE Imagequant LAS 4000, and the exposure time was 2 min. Each experiment was done on at least three pieces of the Teflon based substrate, and each substrate was fabricated with a (4×4)×4 array. The result was calculated from all the data.

For all the concentrations of secondary antibody solution, stronger signals were detected for the 37° C. over the room temperature incubation condition. Especially for the 20 ng/ml secondary antibody solution, relatively strong signal intensity could be detected after the 37° C. incubation, while no signal was detected after room temperature incubation (FIG. 10a). The result demonstrated higher protein-protein interaction reaction rate under relatively higher temperature, and guaranteed lower detection limitation with shorter incubation time. We then measured the nitrocellulose background signal after incubation under the same condition as for the FEP based substrate (FIG. 10b). Nitrocellulose showed strong nonspecific protein adsorption at the 37° C. incubation condition. The adsorption could be reduced a lot if the reaction was done under room temperature, yet the value was still rather high compared with the FEP based substrate.

Example 7: Peptide Microarray Analysis

We have demonstrated the zero nonspecific protein adsorption property of the FEP based substrate, and then we tested if our substrate would be also applicable for peptide microarray analysis (FIG. 11a). A FITC labeled peptide with the sequence KKKKRGD (SEQ ID NO: 1) (named peptide 1 in FIG. 11b) was synthesized and purified. The peptide solution was deposited onto the polydopamine microspots using the droplet rolling method described in Example 3 and incubated overnight under 4° C. Different concentrations of the peptide 1 solution were used to test the conjugation efficiency of the peptide to the substrate (FIG. 11b). From the confocal microscope image, we saw the successfully conjugation of the peptide onto the microspots. Besides, since the peptide is amine group rich, the peptide conjugation was saturated when the concentration was 200 µg/ml.

To perform the peptide microarray analysis, the peptide sflag (sequence: KCIVEVIDYKDDDDK) (SEQ ID NO: 2) was immobilized onto the polydopamine microspots. The anti-flag antibody (Abcam plc) was the target protein to be detected. As shown in FIG. 11a, different concentrations of anti-flag antibody solution were firstly incubated with the peptide microarray. The substrate was then washed thoroughly, followed by the incubation with the HRP labeled anti-flag secondary antibody (Beijing Dingguo Changsheng Biotechnology Co., Ltd.). All the incubation was performed under 37° C. for 30 min. After the applying of the luminol solution and 2 min exposure, the chemiluminescent signal was collected (FIG. 11c). The signal increased exponentially as the concentration increased, and the detected concentration limitation for the antibody was 40 ng/ml. The background signal for the peptide experiments was also nearly zero, and the target signal from the microspots was consistent for the FEP substrates fabricated from different batches under the same experimental condition. The results demonstrated the superior repeatability of the FEP based peptide microarray analysis.

In conclusion, we have successfully fabricated the protein or peptide microarray on FEP substrate for protein analysis. Simple dispensing method was used to deposit sample solutions onto the polydopamine microspots. No complicated surface modification was needed either to activate the microspots or deactivate the background area. Protein or peptide samples could form covalent bonding with polydopamine and be conjugated onto the microspots.

The experiments of both protein and peptide microarray have demonstrated the nonspecific protein adsorption on the background area of the substrate was very low, for example, zero background signal as shown in Examples 6 and 7. Additionally, the target signals from different pieces of substrates showed good repeatability and guaranteed the stability of using the FEP based substrate for more complicated analysis systems.

All publications, patents and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

REFERENCES (1) Plunkett, R. J., Tetrafluoroethylene polymers. U.S. Pat. No. 2,230,654, 1941.
(2) Lee, H.; Dellatore, S. M.; Miller, W. M.; Messersmith, P. B. *Science* 2007, 318, 426.
(3) Chang, T. W. *J Immunol Methods* 1983, 65, 217.
(4) Chang, T. W. In *USPTO*; Centocor, I., Ed. U.S. Pat. No. 4,591,570, 1983.
(5) Chang, T. W. In *USPTO*; Tanox Biosystems, Inc. U.S. Pat. No. 4,829,010, 1987.
(6) Chang, T. W. In *USPTO*; Tanox Biosystems, Inc. U.S. Pat. No. 5,100,777, 1987.
(7) Schena, M.; Shalon, D.; Heller, R.; Chai, A.; Brown, P. O.; Davis, R. W. *P Natl Acad Sci USA* 1996, 93, 10614.
(8) Cretich, M.; Damin, F.; Pirri, G.; Chiari, M., Protein and peptide arrays: Recent trends and new directions. Biomolecular Engineering 2006, 23 (2-3), 77-88.
(9) Espina, V.; Mehta, A. I.; Winters, M. E.; Calvert, V.; Wulfkuhle, J.; Petricoin, E. F.; Liotta, L. A., Protein microarrays: Molecular profiling technologies for clinical specimens. Proteomics 2003, 3 (11), 2091-2100.
(10) Zhu, H.; Bilgin, M.; Bangham, R.; Hall, D.; Casamayor, A.; Bertone, P.; Lan, N.; Jansen, R.; Bidlingmaier, S.; Houfek, T.; Mitchell, T.; Miller, P.; Dean, R. A.; Gerstein, M.; Snyder, M., Global analysis of protein activities using proteome chips. Science 2001, 293 (5537), 2101-2105.
(11) Kusnezow, W.; Hoheisel, J. D., Solid supports for microarray immunoassays. Journal of Molecular Recognition 2003, 16 (4), 165-176.
(12) Nagl, S.; Schaeferling, M.; Wolfbeis, O. S., Fluorescence analysis in microarray technology. Microchim Acta 2005, 151 (1-2), 1-21.
(13) MacBeath, G.; Schreiber, S. L., Printing proteins as microarrays for high-throughput function determination. Science 2000, 289 (5485), 1760-1763.
(14) Nielsen, U. B.; Geierstanger, B. H., Multiplexed sandwich assays in microarray format. Journal of Immunological Methods 2004, 290 (1-2), 107-120.
(15) Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S., Quantum dots for live cells, in vivo imaging, and diagnostics. Science 2005, 307 (5709), 538-544.
(16) Gao, X. H.; Nie, S. M., Quantum dot-encoded mesoporous beads with high brightness and uniformity: Rapid readout using flow cytometry. Anal Chem 2004, 76 (8), 2406-2410.
(17) Wiese, R., Analysis of several fluorescent detector molecules for protein microarray use. Luminescence 2003, 18 (1), 25-30.
(18) Kingsmore, S. F., Multiplexed protein measurement: technologies and applications of protein and antibody arrays. Nature Reviews Drug Discovery 2006, 5 (4), 310-320.
(19) Rusmini, F.; Zhong, Z.; Feijen, J., Protein immobilization strategies for protein biochips. Biomacromolecules 2007, 8 (6), 1775-1789.
(20) Srivastava, S.; LaBaer, J., Nanotubes light up protein arrays. Nat Biotechnol 2008, 26 (11), 1244-1246.
(21) Pirri, G.; Chiari, M.; Damin, F.; Meo, A. *Anal Chem* 2006, 78, 3118.
(22) Sethi, D.; Kumar, A.; Gandhi, R. P; Kumar, P.; Gupta, K. C. *Bioconjugate Chem* 2010, 21, 1703.
(23) Owens, D. E.; Peppas, N. A., Opsonization, biodistribution, and pharmacokinetics of polymeric nanoparticles. Int J Pharmaceut 2006, 307 (1), 93-102.
(24) Jeyachandran, Y L.; Mielczarski, J. A.; Mielczarski, E.; Rai, B., Efficiency of blocking of non-specific interaction of different proteins by BSA adsorbed on hydrophobic and hydrophilic surfaces. J Colloid Interf Sci 2010, 341 (1), 136-142.
(25) Hsieh, H. Y; Wang, P. C.; Wu, C. L.; Huang, C. W.; Chieng, C. C.; Tseng, F. G, Effective Enhancement of Fluorescence Detection Efficiency in Protein Microarray Assays: Application of a Highly Fluorinated Organosilane as the Blocking Agent on the Background Surface by a Facile Vapor-Phase Deposition Process. Anal Chem 2009, 81 (19), 7908-7916.

(26) Lee, J. H.; Kopecek, J.; Andrade, J. D., Protein-resistant surfaces prepared by PEO-containing block copolymer surfactants. J Biomed Mater Res 1989, 23 (3), 351-368.
(27) Shultz, M. A.; Ohdera, A.; MacManiman, J.; McGrath, C. M., Optimized Blocking Of Porous Nitrocellulose Films For Sensitive Protein Microarrays. Biotechniques 2013, 54 (4), 223-225.
(28) Glazer, A. N., Bioconjugate techniques—Hermanson, G T. Nature 1996, 381 (6580), 290-290.
(29) Duffy, D. C.; McDonald, J. C.; Schueller, O. J. A.; Whitesides, G M. *Anal Chem* 1998, 70, 4974.
(30) Xia, Y N.; Whitesides, G. M. *Angew Chem Int Edit* 1998, 37, 551.
(31) Unger, M. A.; Chou, H. P.; Thorsen, T.; Scherer, A.; Quake, S. R. *Science* 2000, 288, 113.
(32) Monahan, J.; Gewirth, A. A.; Nuzzo, R. G., A method for filling complex polymeric microfluidic devices and arrays. Anal Chem 2001, 73 (13), 3193-3197.
(33) Zhou, X.; Lau, L.; Lam, W. W. L.; Au, S. W. N.; Zheng, B. Anal Chem 2007, 79, 4924.
(34) Lynge, M. E.; van der Westen, R.; Postma, A.; Stadler, B. *Nanoscale* 2011, 3, 4916.
(35) Vogelstein, B.; Kinzler, K. W. *P Natl Acad Sci USA* 1999, 96, 9236
(36) Lee, H.; Rho, J.; Messersmith, P. B., Facile Conjugation of Biomolecules onto Surfaces via Mussel Adhesive Protein Inspired Coatings. Adv Mater 2009, 21 (4), 431-434.
(37) Ye, Q.; Zhou, F.; Liu, W. M., Bioinspired catecholic chemistry for surface modification. Chem Soc Rev 2011, 40 (7), 4244-4258.
(38) Dreyer, D. R.; Miller, D. J.; Freeman, B. D.; Paul, D. R.; Bielawski, C. W., Perspectives on poly(dopamine). Chem Sci 2013, 4 (10), 3796-3802.
(39) Han, Z. Y; Chang, Y Y.; Au, S. W. N.; Zheng, B. *Chem Commun* 2012, 48, 1601.
(40) Tang, X. J.; Zheng, B. *Analyst* 2011, 136, 1222.
(41) Zhou, X. C.; Li, J. F.; Wu, C.; Zheng, B. *Macromol Rapid Comm* 2008, 29, 1363.
(42) Han, Z.; Tang, X.; Zheng, B. *J Micromech Microeng* 2007, 17, 1828.

What is claimed is:

1. A microarray substrate, comprising a piece of fluoropolymer whose surface is modified with polydopamine, wherein the polydopamine forms an array of microspots on the surface of the fluoropolymer piece by a microfluidic system, and wherein the microfluidic system comprises a channel layer containing microchannels in which a solution can continuously flow, and a bottom layer which contains an array of micropores and is under the channel layer.

2. The microarray substrate of claim 1, wherein the fluoropolymer piece is made of a fluoropolymer material selected from the group consisting of FEP (fluorinated ethylene propylene), PTFE (polytetrafluoroethylene) and PFA (perfluoroalkoxy).

3. The microarray substrate of claim 1, wherein the microspots serve as the reaction sites for microarray analysis.

4. The microarray substrate of claim 1, wherein the polydopamine is functionalized by a functionalization agent selected from the group consisting of thiol and amino groups.

5. The microarray substrate of claim 1, wherein the polydopamine allows immobilization of proteins, peptides, nucleic acids, oligonucleotides, cells, polymers, small probe molecules or micro/nanoparticles.

6. The microarray substrate of claim 1, wherein the microarray substrate further comprises a support material underneath the fluoropolymer piece.

7. A microarray comprising the microarray substrate of claim 1.

8. The microarray of claim 7, wherein biomolecules, cells and/or micro/nanoparticles are immobilized on the microarray substrate.

9. The microarray of claim 8, wherein the biomolecules are selected from the group consisting of proteins, peptides, nucleic acids, oligonucleotides, polymers and small probe molecules.

10. The microarray of claim 8, wherein the cells are attached to the polydopamine, and the microarray is used for

SEQUENCE LISTING

<160> NUMBER OF SEQ ID NOS: 2

<210> SEQ ID NO 1
<211> LENGTH: 7
<212> TYPE: PRT
<213> ORGANISM: artificial sequence
<220> FEATURE:
<223> OTHER INFORMATION: FITC peptide

<400> SEQUENCE: 1

Lys Lys Lys Lys Arg Gly Asp
1               5

<210> SEQ ID NO 2
<211> LENGTH: 15
<212> TYPE: PRT
<213> ORGANISM: artificial sequence
<220> FEATURE:
<223> OTHER INFORMATION: sflag

<400> SEQUENCE: 2

Lys Cys Ile Val Glu Val Ile Asp Tyr Lys Asp Asp Asp Asp Lys
1               5                   10                  15 performing tissue engineering, stem cell differentiation or cell targeted drug efficacy testing.

11. The microarray of claim 8, wherein micro/nanoparticles are modified with a thiol or amino group, and can be conjugated onto polydopamine microspots of the microarray substrate.

12. The microarray of claim 9, wherein the nucleic acids or the oligonucleotides are modified with a thiol or amino group at their ends.

13. A protein or peptide microarray, comprising the microarray substrate of claim 1, and an immobilized protein or peptide onto the polydopamine, wherein the protein or peptide forms covalent bonding with the polydopamine.

14. A method for producing the microarray substrate of claim 1, further comprising dispensing a dopamine solution onto a piece of fluoropolymer.

15. The method of claim 14, wherein the dispensing comprises binding a microfluidic system with the fluoropolymer piece, and keeping the dopamine solution flowing over the surface of fluoropolymer piece which is exposed to the dopamine solution through the micropores of the microfluidic system.

16. A method for preparing the microarray of claim 7, comprising dispensing a reagent of interest onto the microarray substrate of claim 1.

17. The method of claim 16, wherein the dispensing comprises rolling a droplet of the reagent on the surface of the substrate, wherein the reagent can be captured by polydopamine microspots, and thereby forms an array on the substrate surface.

18. The method of claim 16, wherein the dispensing comprises placing a microfluidic system above the substrate surface, and wherein the reagent is introduced into the channels of the microfluidic system and flows over the microspots of the substrate.

19. The method of claim 16, wherein the reagent is selected from the group consisting of proteins, peptides, nucleic acids, oligonucleotides, cells, polymers, small probe molecules and micro/nanoparticles.

20. A method for preparing a protein or peptide microarray of claim 13, comprising dispensing a protein or peptide solution onto the microarray substrate of any claim 1, and incubating the protein or peptide solution, wherein the protein or peptide forms covalent bonding with the polydopamine and is preferably conjugated onto the polydopamine microspots.

21. A method for detecting a substance of interest in a sample using the microarray claim 7, comprising dispensing the sample on the microarray and detecting the binding of the substance of interest and the microarray.

22. The method of claim 21, wherein the substance of interest is selected from the group consisting of proteins, peptides, nucleic acids, oligonucleotides, cells, drug compounds and micro/nanoparticles.

23. The method of claim 21, wherein the binding of the substance and the microarray is detected via colorimetry, fluorescence, luminescence, electrochemical signals, mass spectrometry, or radioactivity signals.

* * * * *